United States Patent
Lindskog (10) Patent No.: US 9,060,730 B2
(45) Date of Patent: Jun. 23, 2015

(54) METHOD AND KIT FOR QUANTIFYING RISK PREDICTOR

(75) Inventor: Sven Lindskog, Stockholm (SE)

(73) Assignee: DENTOSYSTEM SCANDINAVIA AB, Stockholm (SE)

( * ) Notice: Subject to any disclaimer, the term of this patent is extended or adjusted under 35 U.S.C. 154(b) by 0 days.

(21) Appl. No.: 13/519,670

(22) PCT Filed: Dec. 30, 2009

(86) PCT No.: PCT/EP2009/068018
§ 371 (c)(1),
(2), (4) Date: Oct. 9, 2012

(87) PCT Pub. No.: WO2011/079864
PCT Pub. Date: Jul. 7, 2011

(65) Prior Publication Data
US 2013/0052139 A1 Feb. 28, 2013

(51) Int. Cl.
*A61K 49/00* (2006.01)
*A61B 10/00* (2006.01)
*A61B 5/00* (2006.01)

(52) U.S. Cl.
CPC ............... *A61B 5/411* (2013.01); *A61B 5/447* (2013.01); *A61B 10/0035* (2013.01); *A61K 49/0006* (2013.01)

(58) Field of Classification Search
CPC .... A61B 10/0035; A61B 5/411; A61B 5/441; A61K 49/0006
USPC .......................................... 424/9.8; 600/556
See application file for complete search history.

(56) References Cited

U.S. PATENT DOCUMENTS

| | | | | |
|---|---|---|---|---|
| 4,543,964 | A | * | 10/1985 | Breneman ..................... 600/556 |
| 6,340,455 | B1 | * | 1/2002 | Blomlof et al. .............. 424/9.81 |
| 7,137,970 | B1 | * | 11/2006 | Farage .......................... 604/289 |
| 2007/0134725 | A1 | | 6/2007 | Slawin et al. |

FOREIGN PATENT DOCUMENTS

WO WO 2007/059979 5/2007

OTHER PUBLICATIONS

Australian Patent Examination Report No. 1, dated May 31, 2013, in Australian Patent Application No. 2009357531.
International Preliminary Report on Patentability, mailed Apr. 4, 2012 in International Application No. PCT/EP2009/068018.
Smith et al., "Skin Irritation Thresholds in Hairdressers: Implications for the Development of Hand Dermatitis", British Journal of Dermatology, vol. 146, No. 5, May 1, 2002, pp. 849-852, XP55003447, ISSN: 0007-0963.
Sven Lindskog et al.; "Validation of an Algorithm for Chronic Periodontitis Risk Assessment and Prognostication: Analysis of an Inflammatory Reactivity Test and Selected Risk Predictors", Journal of Periodontology, vol. 81, No. 6, Jun. 1, 2010, pp. 837-847, XP 55018780, ISSN: 0022-3492; DOI: 10.1902/jop/2010.090483.
International Search Report for PCT/EP2009/068018, mailed Sep. 27, 2010.

* cited by examiner

*Primary Examiner* — Janet Epps-Smith
*Assistant Examiner* — Courtney Brown
(74) *Attorney, Agent, or Firm* — Nixon & Vanderhye P.C.

(57) ABSTRACT

A method and a kit for quantification of at least one predictor promoting at least one multifactorial disease, intended for use in assessment of the risk for developing or progression of the at least one multifactorial disease for a subject are disclosed. The kit comprises a plurality of reservoir units (320), each reservoir unit (320) being arranged to releasably retain a skin irritation agent adapted to provoke an unspecific inflammatory response of skin. The kit comprises an estimation unit adapted to estimate a quantification of the at least one predictor on basis of an assessment of the at least one predictor performed by a user on basis of an assessment of the degree of severity of the inflammatory response to the skin irritation agent at each of a plurality of skin sites according to a predetermined inflammatory response criteria performed by the user and relative impact of the at least one predictor on the progress of the at least one multifactorial disease.

21 Claims, 5 Drawing Sheets

METHOD AND KIT FOR QUANTIFYING RISK PREDICTOR

This application is the U.S. national phase of International Application No. PCT/EP2009/068018 filed 30 Dec. 2009 which designated the U.S., the entire contents of each of which are hereby incorporated by reference.

TECHNICAL FIELD

The present invention generally relates to risk assessment for developing or progression of at least one multifactorial disease. In particular, the present invention relates to a method and a kit for estimation of a quantification of at least one predictor promoting at least one multifactorial disease for use in an assessment of the risk for developing or progression of the at least one multifactorial disease in a subject.

BACKGROUND

In today's health care, maintaining health and preventing outbreak of disease is a primary goal. In this regard, both preventive measures to be taken and measures for treatment are in general important, especially for multifactorial diseases, which are largely brought about by the present life style. By multifactorial diseases it is referred to diseases involving or depending on by several factors or causes, for example pertaining to a condition or disease resulting from the interaction of many different genes. One of the problems in modern health care is to identify individuals at risk and to prognosticate their disease outcome, which naturally may be associated with difficulties with regards to achieving a relatively high identification accuracy and/or predictive power, especially when it comes to multifactorial diseases.

As a specific example, periodontitis is a multifactorial infectious disease in patients with a polygenetic predisposition. Predictors from three categories (primary etiological, host, and modifying predictors) interact to reinforce or attenuate the effects of each other. They influence growth and/or composition of an indigenous pathogenic bacterial plaque or biofilm that has been identified as the primary etiological predictor of periodontal disease (which biofilm in turn elicits an inflammatory response), or the inflammatory response itself. However, there are also host predictors as well as a number of predictors that influence the patient's susceptibility to periodontal disease and modify disease progression. When predictors such as these accumulate and work in synergy, episodes of disease development or progression may occur. Consequently, because of the complex nature of the disease, unaided risk assessment and/or prognostication of periodontitis generally exhibit significant variability between different clinicians carrying out these procedures.

Similarly, unaided risk assessment and/or prognostication of other multifactorial diseases, associated with respective predictors that generally interact to reinforce or attenuate the effects of each other, generally exhibit significant variability between different clinicians carrying out these procedures.

In order to obtain a relatively high accuracy and/or predictive power in schemes for risk assessment and/or prognostication of development or progress of multifactorial diseases, such schemes generally require identifying and taking into account several predictors that influence the patient's susceptibility to disease and modify disease progression.

SUMMARY

It is with respect to the above considerations and others that the present invention has been made. The present invention seeks to mitigate, alleviate or eliminate one or more of the above-mentioned deficiencies and disadvantages singly or in combination. In particular, the inventor has realized that it would be desirable to achieve means for estimating a quantification of at least one predictor promoting at least one multifactorial disease, such that the at least one predictor enables achieving a clinically significant contribution to the quality of analysis of the risk for developing or progression of the at least one multi-factorial disease in a subject. As a specific example, the inventor has realized that it would be desirable to achieve such means such that the at least one predictor enables achieving a clinically significant contribution to the quality of analysis of the risk for developing or progression of periodontitis by acting as an adjunct to risk assessment and/or prognostication of periodontitis with the risk assessment scheme. A non-limiting example of which comprises DentoRisk™ (see international patent application no. EP2009/055590).

To achieve this a method and a kit having the features as defined in the independent claims are provided. Further advantageous embodiments of the present invention are defined in the dependent claims.

According to a first aspect of the present invention, there is provided a method for estimating a quantification of at least one predictor promoting at least one multi-factorial disease, the at least one predictor being intended for use in assessment of the risk for developing or progression of the at least one multi-factorial disease in a subject. The method comprises applying a skin irritation agent in a plurality of skin surface concentrations at a plurality of corresponding skin sites of the subject for a predetermined period of time. The skin irritation agent is adapted to provoke an unspecific inflammatory response of skin. The degree of severity of the inflammatory response to the skin irritation agent at each skin site according to a predetermined inflammatory response criteria is assessed. On basis of the assessment of the degree of severity of inflammatory response at each skin site, the at least one predictor is assessed. On basis of the assessment of the at least one predictor, and relative impact of the at least one predictor on the progress of the at least one multi-factorial disease, a quantification of the at least one predictor is estimated.

According to a second aspect of the present invention, there is provided a kit for quantification of at least one predictor promoting at least one multifactorial disease, the kit being intended for use in assessment of the risk for developing or progression of the at least one multifactorial disease for a subject. The kit comprises a plurality of reservoir units. Each reservoir unit is arranged to releasably retain a skin irritation agent. The skin irritation agent is adapted to provoke an unspecific inflammatory response of skin. The reservoir units are arranged such as to enable, when applied to respective skin sites of the subject, application of skin irritation agent in a plurality of skin surface concentrations at the respective skin sites for a predetermined period of time. The kit comprises an estimation unit adapted to estimate a quantification of the at least one predictor on basis of at least two parameters. The at least two parameters comprises an assessment of the at least one predictor performed by a user, on basis of an assessment of the degree of severity of the inflammatory response to the skin irritation agent at each skin site according to a predetermined inflammatory response criteria performed by the user. The at least two parameters comprise relative impact of the at least one predictor on the progress of the at least one multifactorial disease.

The inventor has realized that the results from skin provocation tests using a skin irritant such as sodium lauryl sulphate (SLS) advantageously can be utilized for estimating a measure, or quantification, of a predictor promoting at least one multifactorial disease, for example periodiontitis. Such a predictor may subsequently be utilized in assessment of the risk for developing or progression of the multifactorial disease for a subject. Thus, the present invention is based on the insight that the results from skin provocation tests, wherein the skin irritant comprises SLS, can be utilized for estimating a measure, or quantification, of a predictor promoting periodiontitis, which measure or quantification enables achieving a clinically significant contribution to the quality of analysis of the risk for developing or progression of periodontitis. This has been clinically validated as demonstrated in the example following below (Example 1).

It is also contemplated that the same or similar results as described herein are achievable by means of skin irritation agents other than SLS. As already indicated in the foregoing, the skin irritation agent should be capable of provoking an unspecific inflammatory response. Thus, the skin irritation agent may for example be selected from a group comprising SLS, a ceragenin, a non-allergenic substance, an adjuvant, a non-endogeneous substance, a non-allergenic non-endogeneous substance or a combination thereof.

The skin irritation agent may comprise a skin permeation enhancing component or substance. In this manner, no separate means for enabling introduction of the skin irritation agent into the skin may be necessary and/or the penetration of the skin irritation agent into the skin may be faciliated.

Although the applicant does not wish to be bound by any theory, it is also contemplated that the predictor quantification scheme in accordance with the present invention also can be useful in conjunction with schemes for risk assessment and/or prognostication of development or progress of multi-factorial diseases other than periodontitis, such as gingivitis, chronic periodontitis, diabetes, chronic obstructive pulmonary disease, cardiovascular disease such as atherosclerosis, psoriasis or a combination thereof. In fact, although the applicant does not wish to be bound by any theory, it is contemplated that a predictor quantification scheme in accordance with the present invention can be useful in conjunction with schemes for risk assessment and/or prognostication of development or progress of any multi-factorial disease associated with an impaired inflammatory reactivity in the subject.

The subject can be human. It is also contemplated that the subject can be an animal.

As indicated in the foregoing, the multifactorial disease may be a multi-factorial disease associated with an impaired inflammatory reactivity in a subject suffering from the disease.

The predictor may be intended for use in conjunction with other predictors promoting the at least one multifactorial disease in the assessment of the risk for developing or progression of the at least one multifactorial disease in the subject.

The step of assessment of the degree of severity of the inflammatory response to the skin irritation agent at each skin site according to the predetermined inflammatory response criteria may be performed on a condition that a predetermined second period of time has lapsed, subsequent to the step of application of the skin irritation agent in a plurality of skin surface concentrations at a plurality of corresponding skin sites of the subject for the predetermined first period of time.

In other words, the inflammatory reaction/response may be assessed subsequent to a predetermined second period of time has lapsed after the predetermined first period of time during which the skin irritation agent is applied in a plurality of skin surface concentrations at a plurality of corresponding skin sites of the subject. In this manner, the assessment of the inflammatory reaction/response may be faciliated as redness etc. of the skin caused by a reservoir unit or the like holding the skin irritation agent closely contacting the skin for a relatively long time may be reduced or even eliminated. In turn, this may improve the accuracy of the assessment of the degree of severity of the inflammatory response to the skin irritation agent.

The inflammatory response criteria may for example comprise the number of negative reactions to progressively lower surface concentrations of skin irritation agent with regards to the skin sites.

In the context of some embodiments of the present invention, by "negative reaction" it is referred to as no or with regards to skin irritation an insignificant degree of redness, swelling and/or weal, etc. appearing in the skin (test) site as a result of application of skin irritation agent having a predetermined surface concentration to the skin site.

According to a preferred embodiment of the present invention at least one of the plurality of reservoir units may comprise a substance adapted to maintain skin irritation agent comprised in the respective reservoir unit in an active state for a predetermined period of time. In this manner, the reservoir unit may be ready for use 'as it is', i.e. with only limited or even no user intervention at all required when the it is to be used, with regards to activating the skin irritation agent. The above-mentioned substance may for example be selected from a group comprising propylene glycol, ethylene glycol, butylene glycol, propanediol, a poliol and a combination thereof or another suitable substance substantially void of water. Such a selection enables storing the kit, or specifically the reservoir units, for a relatively long time during which skin irritation agent comprised in one more of the reservoir units is in an active state.

Alternatively or optionally, the kit may comprise at least one activation unit, or at least one so called vehicle, adapted to transform at least one skin irritation agent which is in an inert state into an active state. The at least one activation unit can be adapted to selectively transform at least one skin irritation agent which is in an inert state into an active state.

An inert state of a substance is in general more stable with regards to storage compared to the substance being in an active state (however, see the embodiment of the present invention described in the foregoing).

A configuration such as described immediately in the foregoing may enable storing the skin irritation agent, for example comprised in a kit as described in the foregoing, for relatively long period of time before actually being used. Only in connection with or even immediately foregoing actual application of the skin irritation agent on the skin sites the skin irritation agent may be transformed into an active state.

In the context of some embodiments of the present invention, by "vehicle" it is referred to a means adapted to deliver an active substance to the desired location, for example on the subject.

The predetermined first period of time may be selected within the range of about 18 to 30 hours. For example, the first predetermined of time may be selected within the range of about 23 to 25 hours. The length of such periods of time allows time for the acute phase inflammation to subside and the chronic phase to develop.

A substance, which is substantially inert at least with regards to inducing skin irritation, may be applied to at least one skin site of the subject for the predetermined first period of time concurrently with the application of the skin irritation agent. The predetermined inflammatory response criteria may comprise exhibiting an inflammatory response different from the inflammatory response at the at least one skin site where the above-mentioned substance has been applied.

In this manner, so called negative control of the inflammatory response resulting from application of skin irritation agent may be enabled. The substance may for example comprise a vehicle such as mentioned in the foregoing alone or in combination with another substance.

Depending on the characteristics of the selected skin irritation agent, the vehicle may for example comprise substantially sterile or even completely sterile water.

Alternatively, the vehicle may comprise a substance substantially void of water, such as propylene glycol, ethylene glycol, butylene glycol, propanediol, a poliol, or a combination thereof.

The kit may comprise an adhesive test strip adapted to adhere to skin of the subject, wherein the plurality of reservoir units are arranged on the adhesive test strip and the reservoir units are facing the skin of the subject when the test strip is adhered to the skin of the subject.

Alternatively, the kit may comprise a patch adapted to be releasably attached to skin of the subject, wherein the plurality of reservoir units are arranged on patch and the reservoir units are facing the skin of the subject when the patch is applied to the skin of the subject.

The steps of any method disclosed herein do not have to be performed in the exact order disclosed, unless explicitly stated.

The present invention relates to all possible combinations of features recited in the claims.

Further objects and advantages of the various embodiments of the present invention will be described below by means of exemplifying embodiments.

BRIEF DESCRIPTION OF THE DRAWINGS

Exemplifying embodiments of the invention will be described below with reference to the accompanying drawings, in which.

In the accompanying drawings, the same reference numerals denote the same or similar elements throughout the views.

DETAILED DESCRIPTION

The present invention will now be described more fully hereinafter with reference to the accompanying drawings, in which exemplifying embodiments of the present invention are shown. This present invention may, however, be embodied in many different forms and should not be construed as limited to the embodiments set forth herein; rather, these embodiments are provided by way of example so that this disclosure will convey the scope of the invention to those skilled in the art. Furthermore, like numbers refer to like or similar elements throughout.

Figure 1:
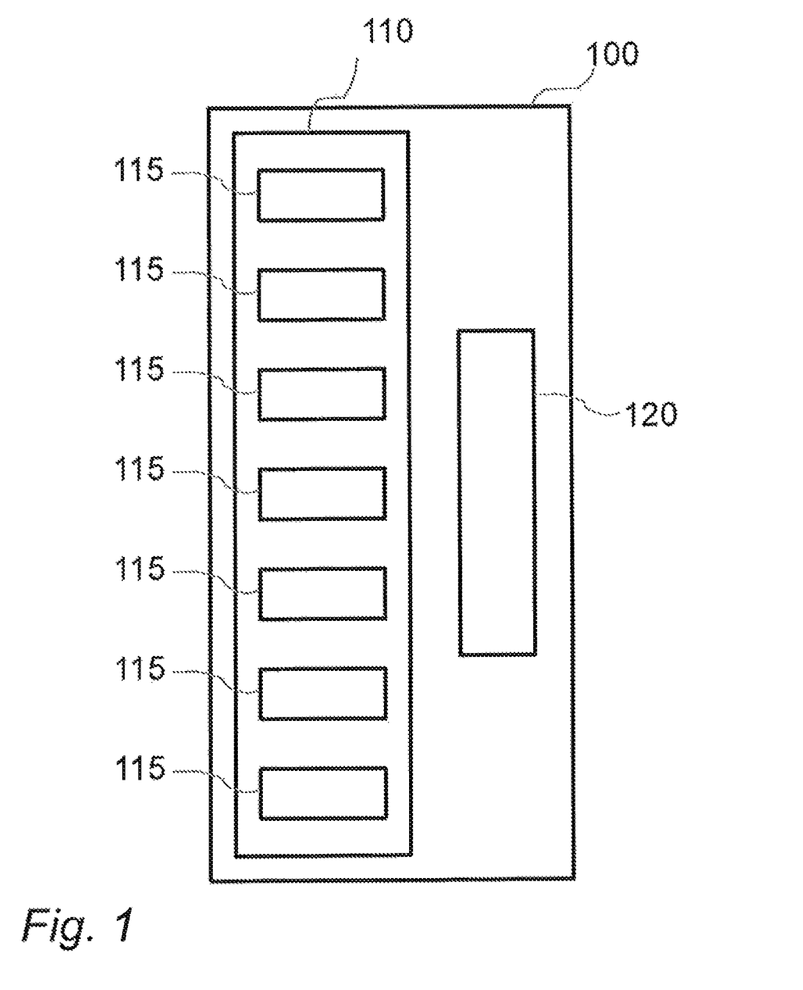
FIG. 1 is a schematic block diagram of a kit for quantification of at least one predictor promoting at least one multi-factorial disease according to an exemplifying embodiment of the present invention, the kit being intended for use in an assessment of the risk for developing or progression of the at least one multifactorial disease for a subject.

Referring now to FIG. 1, there is shown a schematic block diagram of a kit 100 for quantification of at least one predictor promoting at least one multi-factorial disease according to an exemplifying embodiment of the present invention. The kit 100 is intended for use in an assessment of the risk for developing or progression of the at least one multifactorial disease for a subject.

The kit 100 comprises a plurality 110 of reservoir units 115. Each reservoir unit 115 is arranged to releasably retain a skin irritation agent adapted to provoke an unspecific inflammatory response of skin. The kit 100 comprises an estimation unit 120 adapted to estimate a quantification of the at least one predictor on basis of (i) an assessment of the at least one predictor performed by a user on basis of an assessment of the degree of severity of the inflammatory response to the skin irritation agent at each of a plurality of skin sites according to a predetermined inflammatory response criteria performed by a user and (ii) relative impact of the at least one predictor on the progress of the at least one multifactorial disease.

The skin irritation agent comprised in the reservoir units 115 can for example comprise sodium lauryl sulphate (SLS), see the example presented in the following (Example 1).

The estimation unit 120 may for example comprise or be constituted by a processing unit or a computer adapted to access a local or remotely located database or the like by means of wired or wireless communication techniques known in the art, wherein data related to relative impact of the at least one predictor on the progress of the at least one multifactorial disease may be stored. In other words, the estimation unit 120 may be adapted to retrieve data related to relative impact of the at least one predictor on the progress of the at least one multifactorial disease for use in estimating a quantification of the at least one predictor.

Figure 2:
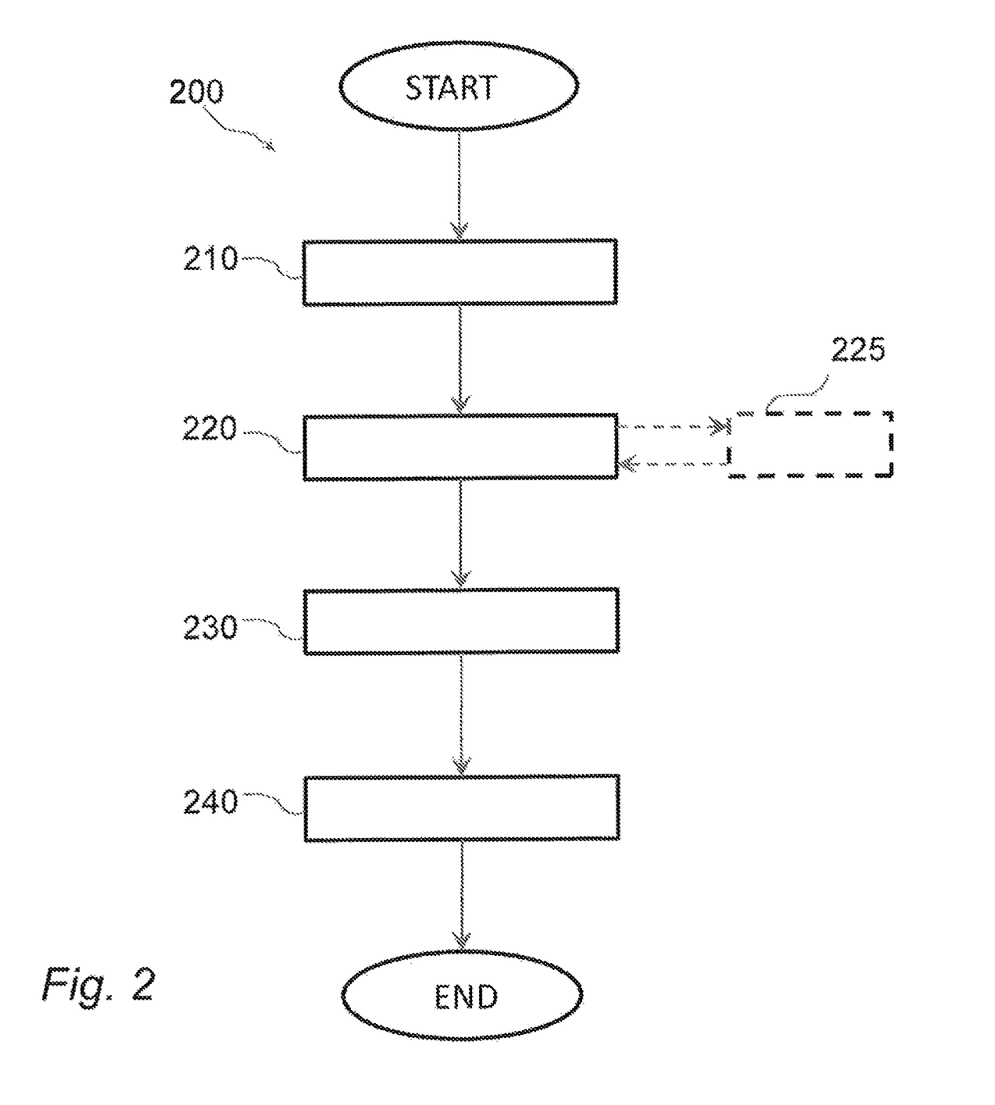
FIG. 2 is a schematic flowchart of a method for estimating a quantification of at least one predictor promoting at least one multifactorial disease according to an exemplifying embodiment of the present invention, the method being intended for use in an assessment of the risk for developing or progression of the at least one multifactorial disease in a subject.

Referring now to FIG. 2, there is shown a schematic flowchart of a method 200 for estimating a quantification of at least one predictor promoting at least one multifactorial disease according to an exemplifying embodiment of the present invention. The method 200 is intended for use in an assessment of the risk for developing or progression of the at least one multi-factorial disease in a subject.

At step 210, a skin irritation agent is applied in a plurality of skin surface concentrations at a plurality of corresponding skin sites of the subject for a predetermined first period of time. The skin irritation agent is adapted to provoke an unspecific inflammatory response of skin.

At step 220, the degree of severity of the inflammatory response to the skin irritation agent at each skin site is assessed according to a predetermined inflammatory response criteria.

At step 230, on basis of the assessment of the degree of severity of inflammatory response at each skin site, the at least one predictor is assessed.

At step 240, on basis of the assessment of the at least one predictor and relative impact of the at least one predictor on the progress of the at least one multifactorial disease, a quantification of the at least one predictor is estimated.

With further reference to FIG. 2, the method 200 may optionally comprise a step 225, comprising applying a substance to at least one skin site of the subject for the predetermined first period of time concurrently with the application of the skin irritation agent, which substance is substantially inert at least with regards to inducing skin irritation, wherein the predetermined inflammatory response criteria comprises exhibiting an inflammatory response different from the inflammatory response at the at least one skin site where the substance has been applied.

Figure 3A:
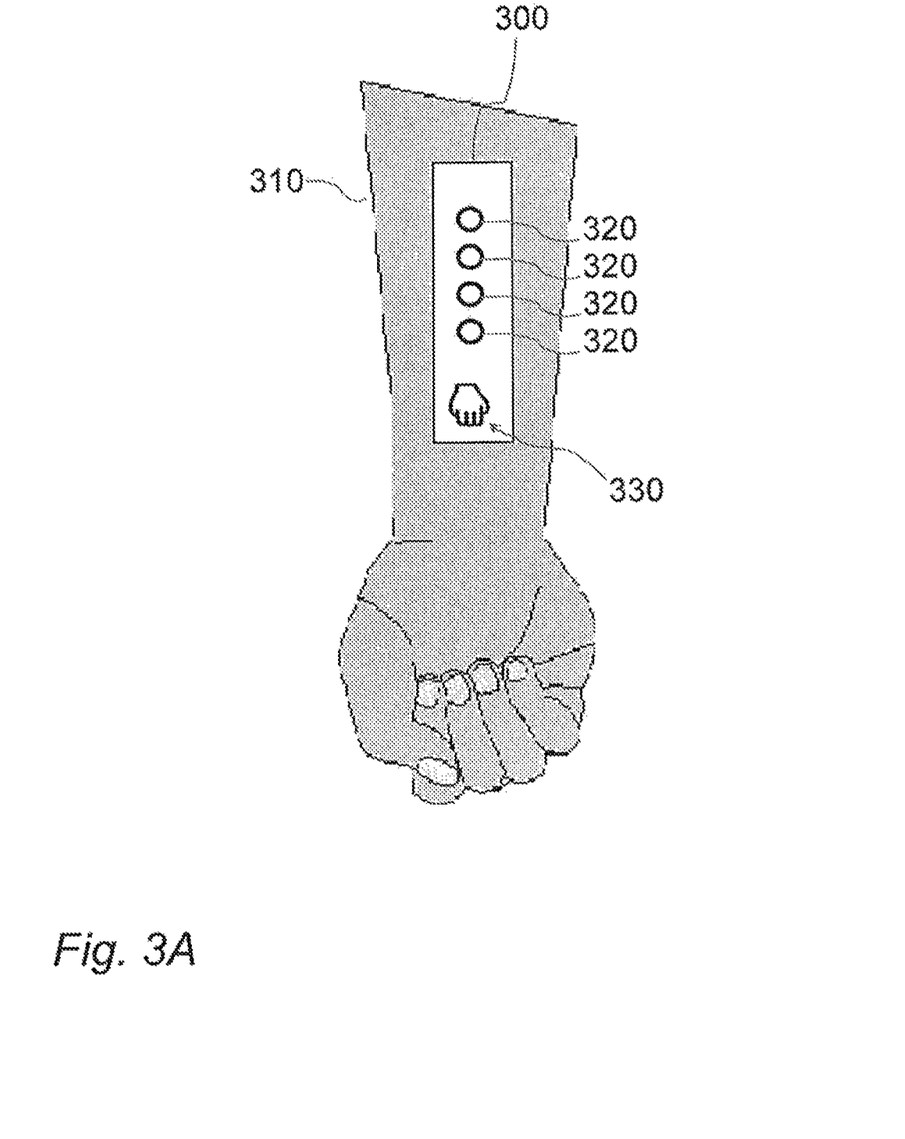
FIG. 3A is a schematic view of an adhesive test strip in accordance with an exemplifying embodiment of the present invention applied to skin on a patient's forearm.

Referring now to FIG. 3A, there is shown a schematic view of an adhesive test strip 300 in accordance with an exemplifying embodiment of the present invention applied to skin on a patient's forearm 310. The adhesive test strip 300 comprises a plurality of reservoir units 320. Each of the reservoir units 320 is arranged to releasably retain a predetermined amount of a skin irritation agent.

The adhesive test strip 300 comprises a marking portion 330 (optional) for facilitating orientation of the adhesive test strip 300 on the patient's skin, for example on the patient's forearm 310 as depicted in FIG. 3A.

Prior to use, the adhesive test strip 300 can be stored in a protective casing or enclosure (not shown in FIG. 3A). The adhesive test strip 300 can be provided with a protective slip (not shown in FIG. 3A) such as a protective piece of paper or the like arranged onto the adhesive portion of the adhesive test strip 300 for mitigating or eliminating adherence of the adhesive portion to objects to which adherence is undesired.

At least one of the reservoir units 320 may comprise a substance adapted to maintain skin irritation agent comprised in the respective reservoir unit in an active state for a predetermined period of time. Thus according to this example a number of reservoir units 320 or all of the reservoir units 320 may be ready for use without further action required to be taken (e.g. without having to take action to transform skin irritation agent from an inert state into an active state, as described in the following with reference to FIGS. 3B and 3C), i.e. ready to be applied at skin of a subject in order to elicit or provoke an unspecific inflammatory response of the skin. The above-mentioned substance may for example be selected from a group comprising propylene glycol, ethylene glycol, butylene glycol, propanediol, a poliol and a combination thereof or another suitable substance substantially void of water. Such a selection enables storing the kit, or specifically storing the reservoir units, for a relatively long time during which skin irritation agent comprised in one more of the reservoir units is in an active state.

Figure 3B:
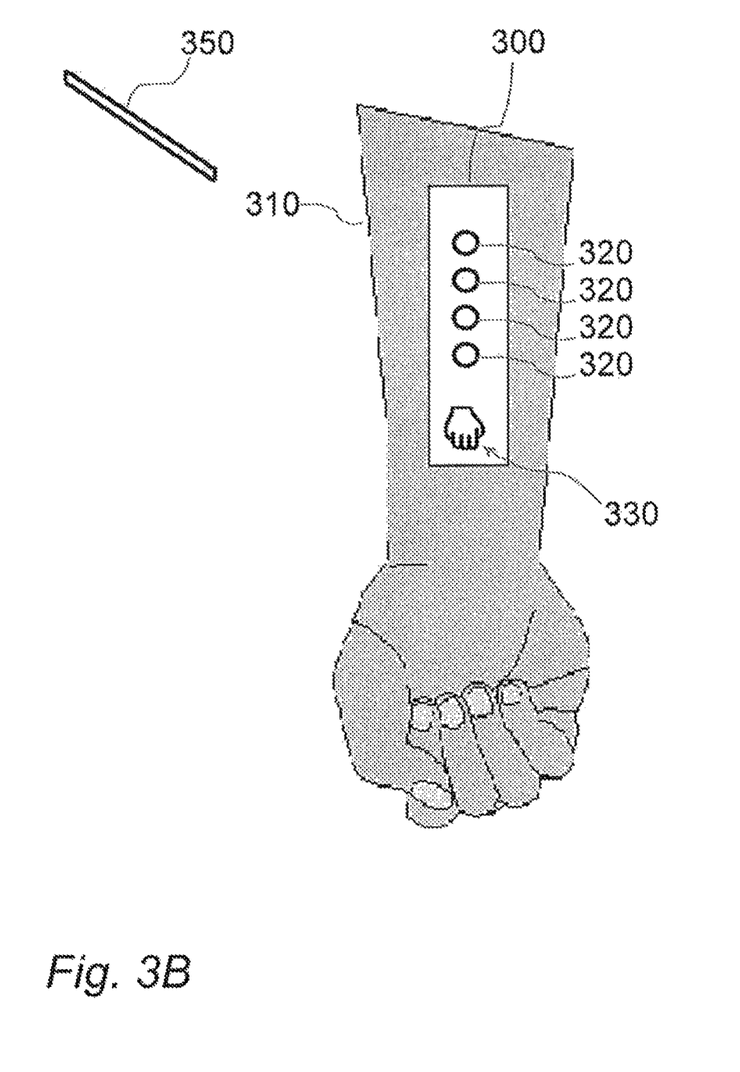
FIG. 3B is a schematic view of an adhesive test strip in accordance with another exemplifying embodiment of the present invention applied to skin on a patient's forearm.

Referring now to FIG. 3B, there is shown a schematic view of an adhesive test strip 300 in accordance with an exemplifying embodiment of the present invention applied to skin on a patient's forearm 310. The adhesive test strip 300 comprises a plurality of reservoir units 320, each of the reservoir units 320 being arranged to releasably retain a predetermined amount of a skin irritation agent.

With reference to FIGS. 3A and 3B, at least one of the reservoir units 320 may for example comprise an absorber, for instance comprising filter material or the like.

With further reference to FIGS. 3A and 3B, a reservoir unit 320 may comprise retainment means (not shown) for providing releasable retainment of skin irritation agent comprised in the reservoir unit 320. Such retainment means may for example comprise an absorber surrounded by a substantially impermeable component such as a silicone ring or the like.

By means of at least one activation unit 350, or vehicle, adapted to selectively transform skin irritation agent being in an inert state into an active state, the skin irritation agent in the reservoir units 320 may be brought into an active state. The activation unit 350 can for example comprise an applicator or pipette 350 containing a predetermined amount of substantially or even completely sterile water, as depicted in FIG. 3B.

The choice of the type of vehicle may depend on the choice of the type of skin irritation agent.

The adhesive test strip 300 comprises a marking portion 330 (optional) for facilitating orientation of the adhesive test strip 300 on the patient's skin, for example on the patient's forearm 310 as depicted in FIG. 3B.

After application of skin irritation agent in the test sites, the general position of each test site may be marked on the skin, for example by means of a ball-point pen or the like, for facilitating assessing the degree of severity of the inflammatory response to the skin irritation agent at each skin site after the adhesive test strip 300 has been removed from the skin.

Prior to use, the adhesive test strip 300 can be stored in a protective casing or enclosure (not shown in FIG. 3B). The adhesive test strip 300 can be provided with a protective slip (not shown in FIG. 3B) such as a protective piece of paper or the like arranged onto the adhesive portion of the adhesive test strip 300 for mitigating or eliminating adherence of the adhesive portion to objects to which adherence is undesired.

As an option or alternative to a pipette 350 such as described above, at least one of the reservoir units 320 may comprise two or more cells (not shown in FIG. 3B) separated by a frangible, substantially impermeable seal (not shown in FIG. 3B), wherein at least one of the cells comprises skin irritation agent and at least one of the cells comprises an activation substance adapted to selectively transform skin irritation agent being in an inert state into an active state. The cells may be arranged such that, when the adhesive test strip 300 is to be used, a user may break the frangible seal so that the activation substance is released into contact with skin irritation agent, thereby transforming the skin irritation agent into an active state. Such a configuration may enable increased ease of use.

Figure 3C:
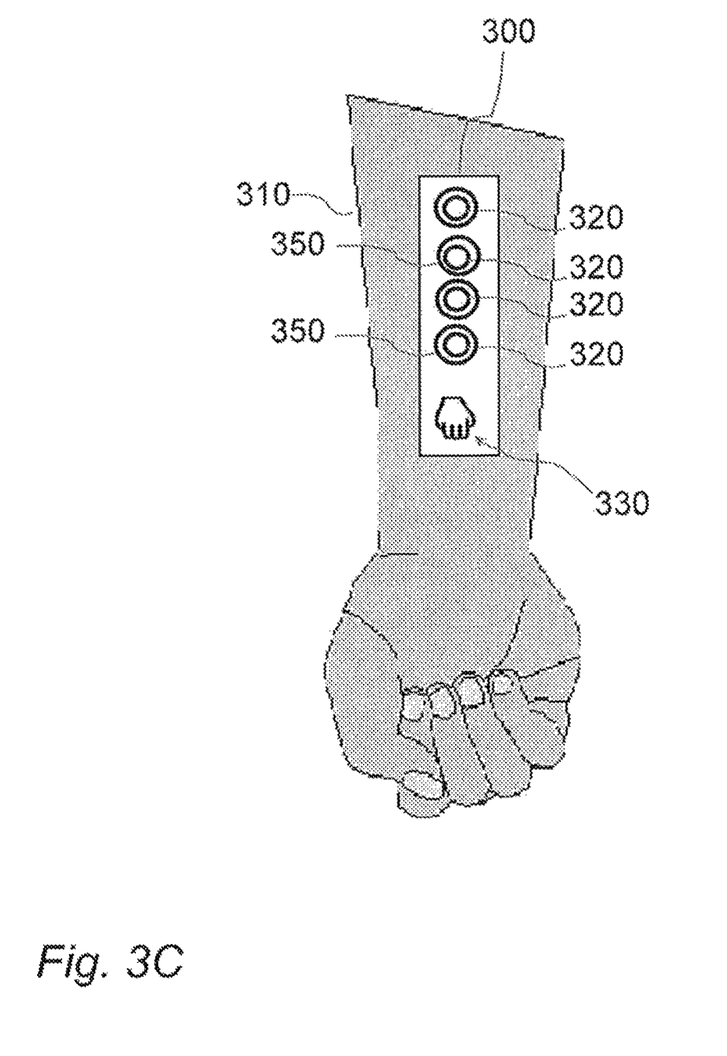
FIG. 3C is a schematic view of an adhesive test strip in accordance with another exemplifying embodiment of the present invention applied to skin on a patient's forearm.

Referring now to FIG. 3C, there is shown a schematic view of an adhesive test strip 300 in accordance with another exemplifying embodiment of the present invention applied to skin on a patient's forearm 310. Identical reference numerals in FIGS. 3A-3C refer to the same or similar elements. Description of such elements with respect to FIG. 3C is therefore omitted. In contrast to FIG. 3B, the adhesive test strip 300 comprises a plurality of activation units 350 (of which only some are referenced by reference numerals in FIG. 3C), each activation unit 350 comprising a substance substantially void of water, such as propylene glycol, ethylene glycol, butylene glycol, propanediol, a poliol, or a combination thereof. This list is not exhaustive.

Some skin irritation agents, such as for example SLS, are unstable in the presence of water or water-containing substances. Thus, a configuration such as depicted in FIG. 3C may enable achieving a kit for quantification of at least one predictor promoting at least one multifactorial disease comprising a plurality of reservoir units arranged to enable, when applied to respective skin sites of the subject, application of skin irritation agent in the active state in a plurality of skin surface concentrations at the respective skin sites for a predetermined period of time, directly to the subject without the use of an applicator or pipette or the like as described with reference to FIG. 3B for transforming skin irritation agent being in an inert state into an active state. This may be possible since the above-mentioned substance, being substantially void of water, may not give rise to instability of the skin irritation agent. In this manner, the adhesive test strip may be ready for use while in storage, without the need for activating the skin irritation agent, which in turn may facilitate or even enable increasing the shelf life of the adhesive test strip.

EXAMPLE 1

Clinical Materials

Three groups of patients were tested with a skin provocation test to assess inflammatory reactivity: Patients with no or negligible periodontal disease (healthy patients), patients suffering from chronic marginal periodontitis but who have responded to treatment (responding patients) and patients suffering from chronic marginal periodontitis but who have responded poorly to treatment (refractory patients). Descriptive statistics for the three patient groups can be found in Tables 1 and 2.

As can be seen from the tables, the three groups of patients represent significantly different levels of periodontal disease while being comparable with respect to age distribution. The two groups of patients with severe periodontitis (responding patients and refractory patients) differ mainly with respect to periodontal pockets depth and percentage of pockets with bleeding on probing indicating that the refractory patients respond poorly to therapy. These latter patients thus, suffer from a more severe form of chronic marginal periodontitis.

TABLE 1

Descriptive statistics for the three patient groups. No significant differences were found between the three groups with respect to mean age (Kruskal Wallis Test). However, responding patients and refractory patients presented with significantly (p < 0.0001) fewer teeth than healthy and responding patients (Kruskal Wallis Test). Standard Deviation in brackets.

| Patient Group | N | % female/male | Mean age (yr) | Mean no. of teeth |
|---|---|---|---|---|
| Healthy individuals | 20 | 85.7/14.3 | 49.8 (7.2) | 28.0 (2.0) |
| Responding patients | 21 | 65.0/35.0 | 53.7 (10.6) | 23.3 (3.8) |
| Refractory patients | 20 | 25.0/75.0 | 51.3 (10.4) | 22.7 (6.4) |

TABLE 2

Clinical characteristics for the three patient groups. Refractory patients and responding patients presented with significantly (p < 0.0001) deeper periodontal pockets, higher mean radiographic bone level and higher mean percentage of periodontal pockets with bleeding on probing than healthy patients (Kruskal Wallis Test). The differences were also significant between refractory and responding patients (p < 0.0001). Standard Deviation in brackets.

| Patient Group | N | Mean periodontal pocket depth (mm) | Mean radiographic marginal bone level (mm) | Mean % of pockets with bleeding on probing |
|---|---|---|---|---|
| Healthy individuals | 20 | 0.19 (0.21) | 1.80 (0.37) | 3.7 (4.3) |
| Responding patients | 21 | 1.80 (0.61) | 4.50 (0.52) | 10.4 (6.7) |
| Refractory patients | 20 | 4.90 (1.21) | 5.30 (0.70) | 46.1 (24.3) |

Testing with the Skin Provocation Test

The skin provocation test comprising an adhesive test strip fitted with four reservoir units (one negative control and three containing progressively increasing doses (200 µg, 100 µg and 50 µg) of sodium dodecyl (laurate) sulphate) was applied to the left forearm in each patient and removed after 24 hours. After an additional 2 hours, the chronic erythematous unspecific inflammatory reaction was assessed. The following definitions applied to reading of the test reactions:

Positive Reaction:

The skin showed an erythematous reaction including oedema, scaling and/or roughness including possible erosions. The size of the reaction does not indicate the severity of symptoms. For a positive reading the reaction must exceed that of the negative control.

Negative Reaction:

No erythematous reaction appeared in the test site.

Results

Results from the three different groups of patients tested with the skin provocation test can be found in Table 3. None of the patients presented any reaction to the negative control.

TABLE 3

Results from testing with the skin provocation test. Refractory patients and responding patients presented with significantly (p < 0.05) fewer positive reactions compared to than healthy patients both as individual groups an as a combined group (Kruskal Wallis Test). Standard Deviation in brackets.

| Patient Group | N | Mean no. of positive reactions |
|---|---|---|
| Healthy individuals | 20 | 1.40 (1.39) |
| Responding patients | 21 | 0.95 (1.28) |
| Refractory patients | 20 | 0.45 (1.20) |

CONCLUSIONS

Patients with severe forms of chronic periodontitis present with varying degrees of decreased inflammatory reactivity as evidenced by the results from testing with the skin provocation test as presented above. This is of clinical significance since the primary objective of the skin provocation test is to contribute to identification of patients at high risk of progression of chronic marginal periodontitis.

While the present invention has been illustrated and described in detail in the appended drawings and the foregoing description, such illustration and description are to be considered illustrative or exemplifying and not restrictive; the present invention is not limited to the disclosed embodiments. Other variations to the disclosed embodiments can be understood and effected by those skilled in the art in practising the claimed invention, from a study of the drawings, the disclosure, and the appended claims. The mere fact that certain measures are recited in mutually different dependent claims does not indicate that a combination of these measures cannot be used to advantage. Any reference signs in the claims should not be construed as limiting the scope.

The invention claimed is:

1. A method for estimating a quantification of at least one predictor promoting at least one multifactorial disease for use in assessment of the risk for developing or progression of the at least one multifactorial disease in a subject, the method comprising:

applying a non-endogenous skin irritation agent in a plurality of skin surface concentrations at a plurality of corresponding skin sites of the subject for a predetermined first period of time, the skin irritation agent being adapted to provoke an unspecific inflammatory response of skin;

transforming the non-endogenous skin irritation agent from an inert state into an active state;

assessing in an estimation unit the degree of severity of the inflammatory response to the activated skin irritation agent at each skin site according to a predetermined inflammatory response criteria;

on basis of the assessment of the degree of severity of inflammatory response at each skin site, assessing in an estimation unit the at least one predictor; and on basis of the assessment of the at least one predictor and relative impact of the at least one predictor on the progress of the at least one multifactorial disease, estimating in an estimation unit a quantification of the at least one predictor.

2. A method for estimating a quantification of at least one predictor promoting periodontitis for use in assessment of the risk for developing or progression of periodontitis in a subject, the method comprising:

applying a non-endogeneous skin irritation agent comprising sodium lauryl sulphate (SLS) in a plurality of skin surface concentrations at a plurality of corresponding skin sites of the subject for a predetermined first period of time, the skin irritation agent being adapted to provoke an unspecific inflammatory response of skin;

transforming the non-endogeneous skin irritation agent from an inert state into an active state;

assessing in an estimation unit the degree of severity of the inflammatory response to the activated skin irritation agent at each skin site according to a predetermined inflammatory response criteria;

on basis of the assessment of the degree of severity of inflammatory response at each skin site, assessing in an estimation unit the at least one predictor; and on basis of the assessment of the at least one predictor and relative impact of the at least one predictor on the progress of periodontitis, estimating in an estimation unit a quantification of the at least one predictor.

3. A method according to claim 1, wherein the a non-endogeneous skin irritation agent comprises:
sodium lauryl sulphate and/or
ceragenin.

4. A method according to claim 1, wherein the assessment of the degree of severity of the inflammatory response to the skin irritation agent at each skin site according to the predetermined inflammatory response criteria is performed on a condition that a predetermined second period of time has lapsed subsequent to the application of the skin irritation agent in a plurality of skin surface concentrations at a plurality of corresponding skin sites of the subject for the predetermined first period of time.

5. A method according to claim 1, wherein the inflammatory response criteria comprises the number of negative reactions to progressively lower surface concentrations of skin irritation agent with regards to the skin sites.

6. A method according to claim 1, wherein the at least one predictor promotes a multifactorial disease associated with an impaired inflammatory reactivity of the subject.

7. A method according to claim 1, wherein the at least one predictor promotes gingivitis, periodontitis, chronic periodontitis, chronic obstructive pulmonary disease, cardiovascular disease, psoriasis or a combination thereof.

8. A method according to claim 1, wherein the predetermined first period of time is selected within the range of about 18 to 30 hours.

9. A method according to claim 8, wherein the predetermined first period of time is selected within the range of about 23 to 25 hours.

10. A method according to claim 9, further comprising applying a substance, the substance being substantially inert at least with regards to inducing skin irritation, to at least one skin site of the subject for the predetermined period of time concurrently with the application of the skin irritation agent, wherein the predetermined inflammatory response criteria comprises exhibiting an inflammatory response different from the inflammatory response at the at least one skin site where said substance has been applied.

11. A method according to claim 1 for estimating a measure, or quantification, of a predictor promoting periodiontitis comprising:

applying a non-endogeneous skin irritation agent to one or more corresponding skin sites of a subject, and transforming the non-endogeneous skin irritation agent from an inert state into an active state.

12. A method according to claim 11, wherein the non-endogeneous skin irritation agent comprises sodium lauryl sulphate (SLS).

13. A kit for quantification of at least one predictor promoting at least one multifactorial disease for use in assessment of the risk for developing or progression of the at least one multifactorial disease for a subject, the kit comprising:

a plurality of reservoir units each reservoir unit releasably retaining a non-endogeneous skin irritation agent adapted to provoke an unspecific inflammatory response of skin;

the reservoir units being arranged such as to enable, when applied to respective skin sites of the subject, application of skin irritation agent in a plurality of skin surface concentrations at the respective skin sites for a predetermined first period of time; the kit further comprising:

an estimation unit configured to estimate a quantification of the at least one predictor on basis of: an assessment of the at least one predictor performed by a user on basis of an assessment of the degree of severity of the inflammatory response to the skin irritation agent at each skin site according to a predetermined inflammatory response criteria performed by the user and relative impact of the at least one predictor on the progress of the at least one multifactorial disease; and at least one activation unit configured to transform at least one skin irritation agent being in an inert state into an active state.

14. A kit according to claim 13, wherein the skin irritation agent comprises:
sodium lauryl sulphate and/or
ceragenin.

15. A kit according to claim 13, wherein at least one of the plurality of reservoir units comprises a substance adapted to maintain skin irritation agent comprised in the respective reservoir unit in an active state.

16. A kit according to claim 13, wherein the activation unit comprises sterile water.

17. A kit according to claim 13, wherein the activation unit comprises a substance void of water.

18. A kit according to claim 17, wherein the activation unit comprises propylene glycol, ethylene glycol, butylene glycol, propanediol, a poliol, or a combination thereof.

19. A kit according to claim 13, further comprising an adhesive test strip configured to adhere to skin of the subject, wherein the plurality of reservoir units are arranged on the adhesive test strip and the reservoir units are facing the skin of the subject when the test strip is adhered to the skin of the subject.

20. A kit according to claim 13, wherein the activation unit includes an applicator or a pipette.

21. A kit according to claim 13, wherein at least one of the reservoir units includes two or more cells separated by a frangible impermeable seal with one of the cells including an activation substance adapted to selectively transform the at least one skin irritation agent from an inert state into an active state.

* * * * *